United States Patent [19]

Inamoto et al.

[11] 4,002,674
[45] Jan. 11, 1977

[54] 4-HOMOISOTWISTANE-3-CARBOXYLIC ACID

[75] Inventors: Yoshiaki Inamoto; Hiroshi Ikeda; Naotake Takaishi, all of Wakayama; Kiyoshi Tsuchihashi, Kainan, all of Japan

[73] Assignee: Kao Soap Co., Ltd., Tokyo, Japan

[22] Filed: July 14, 1975

[21] Appl. No.: 595,556

[30] Foreign Application Priority Data

July 16, 1974 Japan .................... 49-81535

[52] U.S. Cl. .................... 260/514 G; 260/468 G; 260/617 F; 424/317
[51] Int. Cl.² ........................................ C07C 61/12
[58] Field of Search ............ 260/468 G, 514 G, 19

[56] References Cited

OTHER PUBLICATIONS

Fort Jr. et al. Chem Ber. 64, 287, 288(196).
Koch et al. Chem. Ber., 96, 217 (1963).

*Primary Examiner*—Robert Gerstl
*Attorney, Agent, or Firm*—Woodhams, Blanchard and Flynn

[57] ABSTRACT

4-homoisotwistane-carboxylic acid is prepared by reacting 4-homoisotwistane with t-butyl alcohol and formic acid or carbon monoxide, in the presence of sulfuric acid as catalyst.

1 Claim, No Drawings

4-HOMOISOTWISTANE-3-CARBOXYLIC ACID

BACKGROUND OF THE INVENTION

1. Field of the Invention

This invention relates to the compound, 4-homoisotwistane-3-carboxylic acid (II) (tricyclo[5.3.1.0$^{3,8}$]undecane-3-carboxylic acid), and a process for preparing same. More particularly, this invention relates to 4-homoisotwistane-3-carboxylic acid (II) which can be prepared by reacting 4-homoisotwistane (I) (tricyclo[5.3.1.0$^{3,8}$]undecane) with t-butyl alcohol and formic acid or carbon monoxide, in the presence of sulfuric acid as a catalyst. This reaction is represented by the following reaction equation:

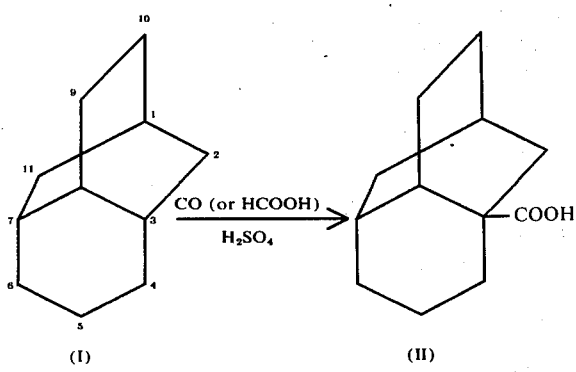

2. Description of the Prior Art

4-Homoisotwistane is a novel tricyclic basket-type hydrocarbon which was recently discovered (Krantz et al, Chem. Commun., 1287 (1971); Majerski et al. Tetrahedron Lett., 4915 (1973); Schleyer et al, Chemistry Lett., 1189 (1973); and the inventors of this application, Chemistry Lett., 1185 (1973)). The properties and activities of this compound are not fully known, but it is known that it can be transformed to 1-methylkyladamantane, a known useful compound, as described in U.S. Ser. Nos. 485,068 and 485,069, both filed July 2, 1974, now U.S. Pat. Nos. 3,894,100 and 3,894,101. No derivatives of this compound have previously been synthesized.

SUMMARY OF THE INVENTION

We have discovered 4-homoisotwistane-3-carboxylic acid of formula II. This compound has biological activity as an antiviral agent, a modifier moiety for various pharmaceutical compounds and a plant hormone. This compound also is useful as an additive for lubricating oils, a high pressure lubricant, a rust-preventive agent and a component of an oiling agent composition for fibers, in the same way as known adamantane compounds. Further, this compound is an intermediate valuable for synthesis of various useful adamantane-type substances. See the section entitled "Adamantane" in the Supplement Volume of Kirk-Othmer's "Encyclopedia of Chemical Technology".

The compound of this invention can be obtained by reacting 4-homoisotwistane (I) with t-butyl alcohol and formic acid or carbon monoxide, in the presence of sulfuric acid. This reaction is included in the category of the so-called Koch's carboxylation reaction, which is known as a reaction useful for obtaining alkane carboxylic acids, especially tertiary alkane carboxylic acids. But, it was not known, prior to our invention, at what position carboxylation will occur when 4-homoisotwistane (I) is subjected to this reaction, and the number of positions at which carboxylation will occur was also unknown, because 4-homoisotwistane (I) had not been subjected to any reaction. We found that the Koch carboxylation reaction occurs selectively at the 3-position of 4-homoisotwistane (I) and only one carboxyl group is introduced into only this 3-position. Based on this discovery, we have completed this invention.

The basis for concluding that the carboxyl group is introduced into only the 3-position of the 4-homoisotwistane to form the 4-homoisotwistane-3-carboxylic acid will now be described.

When 4-homoisotwistane (I) is reacted with t-butyl alcohol alone, in the presence of sulfuric acid, without addition of formic acid, the starting 4-homoisotwistane is not changed at all and it is recovered almost quantitatively. Accordingly, it is proven that under the conditions of the Koch reaction, the skeleton of 4-homoisotwistane (I) is not changed, and it remains as it was at the start.

In the nmr spectrum of 4-homoisotwistane-3-carboxylic acid, only one acidic proton, namely, the proton of the carboxylic acid that disappears on the treatment with heavy water, appears isolatedly in a lower magnetic field. If it is supposed that the carboxyl group is introduced other than at a bridgehead position, namely, at the position of secondary carbon atoms, only 1 proton attached to secondary carbon atom should be isolated from the remaining protons by the influence of the carboxyl group and it should appear on the side of a lower magnetic field. However, in the actual nmr spectrum, only a complex multiplet is observed in the region of δ 2.6–0.8. It is known that in the Koch reaction, the reactivity of tertiary carbon atoms (bridgehead carbon atoms in the case of (I)) is much higher than that of secondary or primary carbon atoms. In view of the foregoing, it can be determined that in the present carboxylic acid, the carboxyl group must be introduced into the 1-position, 3-position (equivalent to the 7-position) or 8-position, and that there is not possibility that the carboxyl group is introduced into a position other than the above three bridgehead position. When the proton nmr of a carbinol (III) of the following formula:

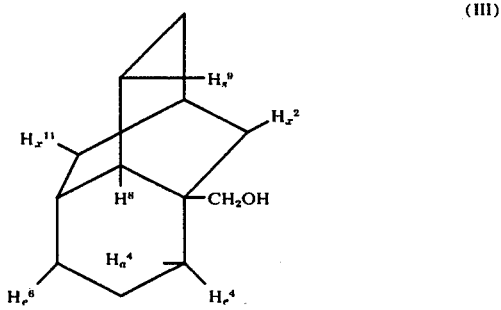

which is prepared by reducing the present carboxylic acid (II) with lithium aluminum hydride, is measured in the presence of tris(dipivaroylmethanate) europium (Eu(dpm)$_3$) while varying the concentration thereof, there is observed the presence of 2 protons and a hydroxy proton attached to the carbinol carbon, 5 different protons which shift greatly toward the side of a low magnetic field with an increase of the concentration of Eu(dmp)$_3$ and 2 different protons which are on the side of a high magnetic field and hardly shift (in addition, there are 10 different protons which are situated between the two groups of protons and these have not been sufficiently analyzed). Among the possible carbinols derived from the three possible kinds of 4-homoisotwistane-carboxylic acids having the carboxyl group at the 1-, 3- or 8-position, only the 3-substituted product would exhibit the above behavior to such a shift reagent. According to the empirical law that the size of the low magnetic field shift of a proton by Eu(dpm)$_3$ is in inverse proportion to the square or cube of the distance between said proton and the Eu atom in the Eu(dpm)$_3$-carbinol complex (Cockerill et al, Tetrahedron Lett., 5145, 5143 (1970) and C. C. Hinckley, J. Amer. Chem. Soc., 91, 5160 (1969)), in the molecular model of Dreiding, the distances of the protons from the Eu atom (it is supposed that the Eu atom is located on an extension of the line connecting the C$_3$ atom of the skeleton to the carbinol carbon, based on the teaching of Cockerill et al, Chem. Rev., 73, 553 (1973)) are estimated. Thus, it is seen that only 5 protons are relatively close to the Eu atom and they are different from one another (it is considered that they correspond to H$_s^9$, H$_x^2$, H$^8$, H$_a^4$ and H$_e^4$ in the formula (II), respectively); and that only two protons are scarcely influenced by the Eu atom and they are different from each other (corresponding to H$_x^{11}$ and H$_e^6$). Only the 3-carbinol compound (II) satisfies the above conditions. Incidentally, since each of the 1-carbinol and 8-carbinol compounds has in the molecule a symmetric face (passing through C$_1$-C$_{10}$-C$_9$-C$_8$-C$_5$), if there were present protons close to the Eu atom, the number of such protons should naturally be an even number.

Also in view of the reactivity of bridgehead carbon atoms (Schleyer et al, J. Amer. Chem. Soc., 93, 3189 (1971)), it can be assured that the 3-carboxylic acid (II) is formed by the Koch reaction of 4-homoisotwistane. If viewed from a different point, the 3-position in the compound of formula (I) is the bridgehead 1-position of bicyclo[3.3.1]nonane in which an ethano bridge is laid between the 3- and 9-positions (see the formula (IV) given below). Further, if viewed from a still different point, the 1- and 8-positions in the formula (I) correspond to the bridgehead 4- and 1-positions of bicyclo[2.2.2.]octane in which a trimethylene bridge is laid between the 2- and 6-positions (see the formula (V) given below). If the influences caused by the ethano and trimethylene bridges are neglected, the reactivity of the 1-position in the formula (IV) is 10$^4$ times as high as the reactivity of the 1- or 4-position in the formula (V).

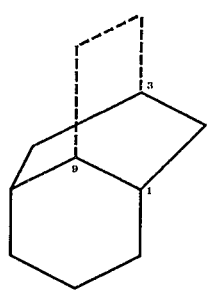

(IV)

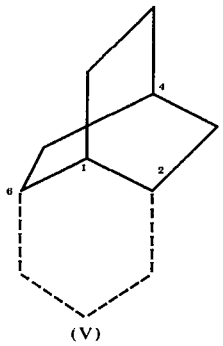

(V)

In practicing the process of this invention, the concentration of the sulfuric acid is 70 to 100%, preferably 85 to 98%. In case the sulfuric acid concentration is lower than 70%, a sufficient hydrogen anion exchange reaction is caused between the starting substance (I) and the t-butyl cation formed from t-butyl alcohol, and the resulting product is mainly composed of pivaric acid. If sulfuric acid having a concentration higher than 100% (fuming sulfuric acid) is employed, oxidation of 4-homoisotwistane (I) is caused simultaneously, resulting in the formation of homoisotwistanones and a reduction of the yield of the desired product. The amount of sulfuric acid varies depending on the amount used of t-butyl alcohol. The minimum amount of sulfuric acid is such that the water formed from t-butyl alcohol and which is equimolar to the t-butyl alcohol used, does not reduce the sulfuric acid concentration below 70%. The upper limit of the amount of sulfuric acid is not critical.

In view of stoichiometry, it is considered to be sufficient that the amount of t-butyl alcohol is equimolar to the amount of the starting substance. However, since the t-butyl cation formed from t-butyl alcohol is not necessarily consumed stoichiometrically for the hydrogen anion exchange reaction, in practice, t-butyl alcohol is used in an amount of 1.2 to 10 moles, preferably 1.5 to 6 moles, per mole of the starting substance (I). When t-butyl alcohol is used in an amount of more than 10 moles per mole of the starting substance, side reactions such as alkylation of 4-homoisotwistane (I) by the t-butyl cation are caused to occur, and the yield of the desired product is reduced.

In case carbon monoxide is used as the carboxylating agent, no bad effect occurs even if it is used in large excess. However, in case formic acid is used, since an equimolar amount of water is formed by decomposition of formic acid by sulfuric acid, it is necessary to adjust the amount of the sulfuric acid as in the case of t-butyl alcohol. The lower limit of the carboxylating agent necessary for the reaction is 1.2 moles, preferably 1.5 moles, per mole of the starting substance (I).

The reaction temperature is from −20° C. to +50° C, preferably from −10° C. to +30° C. At a higher temperature, side reactions are caused to occur by thermal decomposition of the t-butyl cation.

In the process of this invention, since each of the starting substance (I) and the desired product (II) is soluble in sulfuric acid only slightly and each of them is solid at the reaction temperature, it is preferred that a solvent be used. Any solvents which are inert under the reaction conditions, exclusive of those capable of readily providing hydrogen anions (for example, aliphatic hydrocarbons having tertiary carbon, such as isopentane and methylcyclohexane) can be used. For example, there are preferably employed alkanes and cycloalkanes such as n-pentane, n-hexane, n-heptane, cyclopentane and cyclohexane, and halogenated alkanes such as methylene chloride, chloroform and carbon tetrachloride.

The process of this invention can be performed under atmospheric pressure or under elevated pressure. When carbon monoxide is employed, it is preferred that the reaction is carried out under elevated pressure.

This invention will now be further described in detail by reference to the following illustrative Examples.

EXAMPLE 1

A mixture of 15 g (0.10 mole) of 4-homoisotwistane, 100 ml of cyclohexane and 450 g of 95% sulfuric acid was cooled by ice water to maintain the mixture at 10°–15° C., and a solution of 30 g (0.41 mole) of t-butyl alcohol in 55 g (120 moles) of 99% formic acid was added dropwise to the above mixture over a period of 2.5 hours, with agitation. After completion of the dropwise addition, the mixture was further agitated for 3 hours at the same temperature.

The reaction mixture was placed on 1 Kg of ice pieces, and after the organic layer was separated, the water layer was extracted with cyclohexane and the extract was combined with the organic layer. The resulting mixture was washed with water and extracted 3 times with a 1.5% solution of sodium hydroxide.

To the sodium hydroxide extract was added dropwise 35% hydrochloric acid to adjust the pH to 1–2, and the mixture was extracted with diethyl ether. The ether extract was dried over anhydrous sodium sulfate and was fractionated. A fraction boiling at 135°–140° C. under 0.9 mm Hg was collected to obtain 12.5 g (yield = 63%) of crude 4-homoisotwistane-3-carboxylic acid (II).

When the product was allowed to stand still, it solidified to form white crystals. The crystals were sublimed under reduced pressure to obtain a pure product having a melting point of 95°–96° C.

Elemental Analysis Values for $C_{12}H_{18}O_2$: Found: C = 75.0%, H = 9.5%. Calculated: C = 74.19%, H = 9.34%.

ir (neat, $cm^{-1}$): 2940, 2920, 2860, 1680, 1470, 1460, 1450, 1400, 1285, 1275, 1260.

nmr ($CDCl_3$, TMS internal standard, $\delta$): 2.6–0.8 (complex multiplet, 17H); 10.20 (singlet, 1H, disappearing on $D_2O$ treatment).

MS (m/e) (relative intensity, %): 194 ($M^+$, 12), 150 (13), 149 (100), 92 (12), 80 (19), 78 (15), 66 (27), 57 (12), 41 (17).

EXAMPLE 2

The reaction mixture was formed and treated in the same manner as in Example 1 except that carbon tetrachloride was used instead of cyclohexane. The intended product (II) was obtained in an amount of 14.5 g (yield = 73%).

EXAMPLE 3

This example shows that the methyl ester derived from the compound (II) of the present invention has an excellent antiviral property.

Methyl 4-homoisotwistane-3-carboxylate (VI) was prepared by the reaction of the acid (II) with diazomethane (F. Arndt, Organic Syntheses, Collective Volume II, p 165 (1943)). The methyl ester (VI) thus obtained was tested against Newcastle disease virus (NDV) in an in vitro test using chick embryo monolayer tissue culture as follows.

A chick embryo monolayer tissue culture was mixed with NDV solution having a concentration of 128 hemegglutinin aggregation units and with an aqueous suspension of the methyl ester (VI) in the culture, and then cultured at 37° for 48 hours. The concentration of the replicated virus in the resulting tissue culture was determined by a hemagglutination reaction.

| Concentration in the Starting Tissue Culture ($\mu$g/ml) | % Inhibition of NDV Multiplications* | |
| --- | --- | --- |
| | VI | Amantadine . HCl |
| 16 | 99.4 | 0.0 |
| 8 | 91.2 | 0.0 |
| 4 | 0.0 | 0.0 |

*Relative to the control experiment in which no VI or Amantadine . HCl was added.

Thus, the virus replication in the tissue culture containing above 4 $\mu$g/ml of methyl 4-homoisotwistane-3-carboxylate (VI) was almost completely inhibited. This result apparently shows that the antiviral activity of the methyl ester (VI) is extremely superior to that of amantadine hydrochloride which is an established antiviral agent for men and domestic animals.

The methyl ester (VI) also has a potent antiviral activity in vivo. The method of administration and dosages to be employed in the use of the compound (VI) are similar to those conventionally used for representative antiviral agents, and the details can readily be discerned and determined by those who are familiar with the arts in the field.

The embodiments of the invention in which an exclusive property or privilege is claimed are defined as follows:

1. 4-homoisotwistane-3-carboxylic acid.

* * * * *